(12) United States Patent
Van Kruchten et al.

(10) Patent No.: US 8,110,712 B2
(45) Date of Patent: Feb. 7, 2012

(54) PROCESS FOR THE PREPARATION OF ALKYLENE GLYCOL

(75) Inventors: Eugene Marie Godfried Andre Van Kruchten, Amsterdam (NL); Abraham Adriaan Smaardijk, Amsterdam (NL); Hendrik Stichter, Amsterdam (NL)

(73) Assignee: Shell Oil Company, Houston, TX (US)

( * ) Notice: Subject to any disclaimer, the term of this patent is extended or adjusted under 35 U.S.C. 154(b) by 391 days.

(21) Appl. No.: 12/420,564

(22) Filed: Apr. 8, 2009

(65) Prior Publication Data

US 2009/0259077 A1    Oct. 15, 2009

(30) Foreign Application Priority Data

Apr. 10, 2008   (EP) ..................... 08103485

(51) Int. Cl.
*C07C 27/04* (2006.01)

(52) U.S. Cl. .................... 568/852; 568/858; 568/864

(58) Field of Classification Search .................. 568/852, 568/858

See application file for complete search history.

(56) References Cited

U.S. PATENT DOCUMENTS

| 6,080,897 A | 6/2000 | Kawabe | 568/858 |
| 6,187,972 B1 | 2/2001 | Kawabe et al. | 568/858 |

FOREIGN PATENT DOCUMENTS

| GB | 2011402 | 7/1979 |
| WO | WO2007144360 | 12/2007 |
| WO | WO2009021830 | 2/2009 |

*Primary Examiner* — Sikarl Witherspoon

(57) ABSTRACT

The invention provides a process for the preparation of an alkylene glycol from an alkylene oxide. Alkylene oxide reacts with carbon dioxide in the presence of a carboxylation catalyst to provide alkylene carbonate; alkylene carbonate reacts with water in the presence of a hydrolysis catalyst to provide alkylene glycol. An initial charge of the carboxylation catalyst and an initial charge of the hydrolysis catalyst are added, the degradation and activity of the hydrolysis catalyst are monitored, and when the activity of the hydrolysis catalyst has fallen below a minimum level, an additional charge of the hydrolysis catalyst is added.

13 Claims, 1 Drawing Sheet

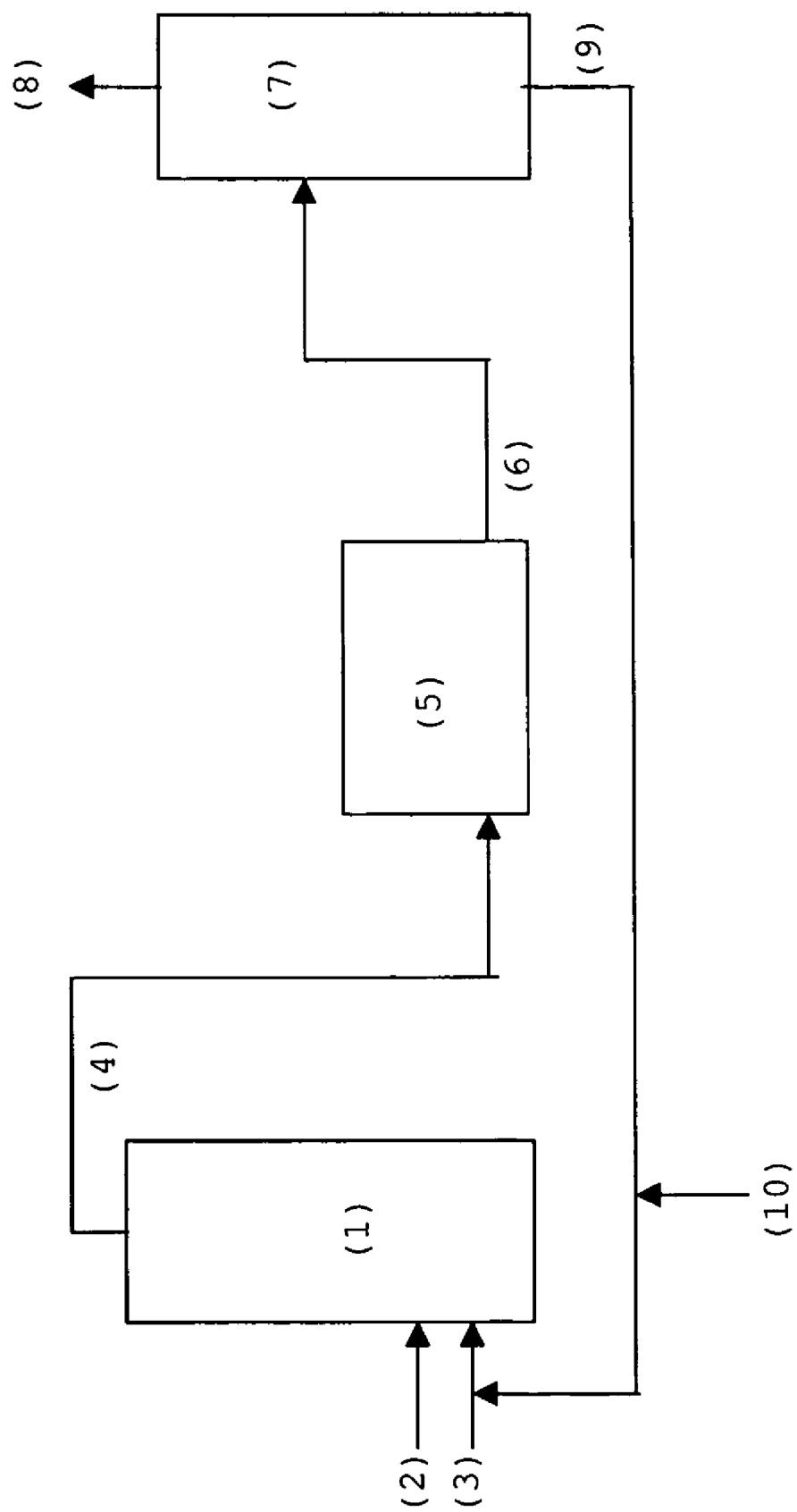

PROCESS FOR THE PREPARATION OF ALKYLENE GLYCOL

FIELD OF THE INVENTION

The present invention relates to a process for the preparation of an alkylene glycol from an alkylene oxide.

BACKGROUND OF THE INVENTION

Monoethylene glycol is used as a raw material in the manufacture of polyester fibres, polyethylene terephthalate (PET) bottles and resins. It is also incorporated into automobile antifreeze liquids.

Monoethylene glycol may be prepared in a highly selective process from ethylene oxide via ethylene carbonate. This is typically carried out in a two-step process wherein the first step is the reaction of ethylene oxide with carbon dioxide to form ethylene carbonate, and the second step is the hydrolysis of ethylene carbonate to form ethylene glycol.

Catalysts may be supplied to the carboxylation and hydrolysis steps to increase both the rate and selectivity of the reaction. WO 2007/144360 discloses a process for the manufacture of alkylene glycol from alkylene oxide via alkylene carbonate, wherein homogeneous carboxylation and hydrolysis catalysts are used. A homogeneous catalyst solution (comprising carboxylation catalyst and hydrolysis catalyst) is separated from crude monoethylene glycol and is recycled back to the carboxylation and hydrolysis reactors.

The present inventors have sought to further improve the manufacture of alkylene glycol from alkylene oxide.

SUMMARY OF THE INVENTION

The present invention provides a process for the preparation of an alkylene glycol from an alkylene oxide, wherein alkylene oxide reacts with carbon dioxide in the presence of a carboxylation catalyst to provide alkylene carbonate, wherein alkylene carbonate reacts with water in the presence of a hydrolysis catalyst to provide alkylene glycol, and wherein the active phase of the hydrolysis catalyst is one or more bases, comprising steps of (a) adding an initial charge of the carboxylation catalyst and an initial charge of the hydrolysis catalyst to catalyse the reaction of alkylene oxide with carbon dioxide, and to catalyse the reaction of alkylene carbonate with water;
(b) monitoring the degradation and activity of the hydrolysis catalyst; and
(c) when the activity of the hydrolysis catalyst has fallen below a minimum level, adding an additional charge of the hydrolysis catalyst, wherein if an additional charge of carboxylation catalyst is added when the additional charge of the hydrolysis catalyst is added, the weight ratio of additional hydrolysis catalyst to additional carboxylation catalyst is at least 5:1.

The inventors have surprisingly discovered that during the process for the preparation of alkylene glycol, a basic hydrolysis catalyst degrades significantly more rapidly than the known carboxylation catalysts under typical conditions. The inventors have also discovered that as the amount of the basic hydrolysis catalyst decreases, there is an increased production of byproducts (e.g. aldehydes, dioxolanes), decreased conversion of alkylene carbonate and decreased selectivity (increased production of dialkylene glycol and higher glycols). Therefore the inventors have devised the process of the invention wherein the degradation and associated activity of the hydrolysis catalyst is monitored and additional hydrolysis catalyst is supplied to the process. By maintaining the amount of the hydrolysis catalyst above a minimum level, the process avoids increased production of byproducts and decreased selectivity. Because the carboxylation catalyst typically degrades much more slowly than the hydrolysis catalyst, additional carboxylation catalyst is not required when the additional charges of hydrolysis catalyst are added. Preferably no additional carboxylation catalyst is added when an additional charge of hydrolysis catalyst is added. (The benefits of the invention can still be achieved if small quantities of carboxylation catalyst are added with the additional hydrolysis catalyst, but a significant excess of hydrolysis catalyst should be added, i.e. the weight ratio of additional hydrolysis catalyst to additional carboxylation catalyst should be at least 5:1.)

BRIEF DESCRIPTION OF THE DRAWINGS

FIG. 1 is a schematic diagram showing a process according to an embodiment of the invention.

DETAILED DESCRIPTION OF THE INVENTION

The present invention provides a process for the preparation of an alkylene glycol from an alkylene oxide, proceeding via an alkylene carbonate intermediate:

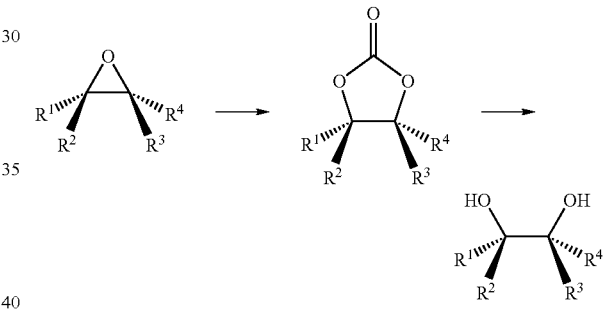

Suitably, $R^1$, $R^2$, $R^3$ and $R^4$ may independently be chosen from hydrogen or an optionally substituted alkyl group having from 1 to 6 carbon atoms, preferably from 1 to 3 carbon atoms. As substituents, moieties such as hydroxy groups may be present. Preferably, $R^1$, $R^2$ and $R^3$ represent hydrogen atoms and $R^4$ represents hydrogen or a non-substituted $C_1$-$C_3$-alkyl group and, more preferably, $R^1$, $R^2$, $R^3$ and $R^4$ all represent hydrogen atoms.

Examples of suitable alkylene oxides therefore include ethylene oxide and propylene oxide. In the present invention the most preferred alkylene oxide is ethylene oxide.

Alkylene oxide reacts with carbon dioxide in the presence of a carboxylation catalyst to provide alkylene carbonate and alkylene carbonate reacts with water in the presence of a hydrolysis catalyst to provide alkylene glycol. Processes for preparing ethylene glycol by this route are described in detail in U.S. Pat. No. 6,080,897, U.S. Pat. No. 6,187,972 and WO 2009/021830, which are all herein incorporated by reference in their entirety. In one embodiment of the invention, the reaction of alkylene oxide with carbon dioxide occurs predominantly in one or more carboxylation reactors, and the reaction of alkylene carbonate with water occurs predominantly in one or more hydrolysis reactors, wherein the one or more hydrolysis reactors are downstream of the one or more carboxylation reactors. Preferably for every 10 moles of alkylene oxide supplied to the one or more carboxylation reactors, at least 5 moles of alkylene carbonate exits the one or more carboxylation reactors. Preferably for every 10 moles of alkylene carbonate supplied to the one or more hydrolysis reactors, at least 5 moles of alkylene glycol exits the one or more hydrolysis reactors. In an alternative embodiment of the invention, the reaction of alkylene oxide with carbon dioxide and the reaction of alkylene carbonate with water occurs predominantly in a single reactor. Preferably for every 10 moles of alkylene oxide supplied to the reactor, less than 2 moles of alkylene carbonate and greater than 6 moles of alkylene glycol exits the reactor.

The carboxylation catalyst may be a heterogeneous or homogeneous catalyst. Homogeneous catalysts that are known to promote carboxylation include alkali metal halides such as potassium iodide and potassium bromide, and halogenated organic phosphonium or ammonium salts such as tributylmethylphosphonium iodide, tetrabutylphosphonium iodide, triphenylmethylphosphonium iodide, triphenyl-propylphosphonium bromide, triphenylbenzylphosphonium chloride, tetraethylammonium bromide, tetramethylammonium bromide, benzyltriethylammonium bromide, tetrabutylammonium bromide and tributylmethylammonium iodide. Heterogeneous catalysts that promote carboxylation include quaternary ammonium and quaternary phosphonium halides immobilized on silica, quaternary ammonium and quaternary phosphonium halides bound to insoluble polystyrene beads, and metal salts such as zinc salts immobilised on solid supports containing quaternary ammonium or quaternary phosphonium groups, such as ion exchange resins containing quaternary ammonium or quaternary phosphonium groups. Preferably the carboxylation catalyst is a homogeneous catalyst, most preferably an organic phosphonium iodide or alkali halide salt.

The active phase of the hydrolysis catalyst is one or more bases. The hydrolysis catalyst may be homogeneous or heterogeneous. Homogeneous catalysts that promote hydrolysis and that have a base as the active phase include hydroxides, bicarbonates, carbonates, carboxylates (e.g. acetates and formates) and phosphates. Examples include potassium hydroxide, sodium hydroxide, potassium bicarbonate, sodium bicarbonate, potassium carbonate, sodium carbonate, potassium acetate, potassium formate, tributylmethyl phosphonium hydroxide, potassium phosphate and disodium hydrogen phosphate. Heterogeneous catalysts that promote hydrolysis and that have a base as the active phase include hydroxide, bicarbonate and carbonate ions immobilised on solid supports, for example hydroxide, bicarbonate or carbonate immobilised on ion exchange resins containing quaternary ammonium or quaternary phosphonium groups; basic alumina; basic zeolite; and poly-4-vinyl-pyridine.

In a preferred embodiment the hydrolysis catalyst has bicarbonate anions as the active phase. Metal carbonates, hydroxides and bicarbonates, such as potassium carbonate, potassium hydroxide and potassium bicarbonate, all provide bicarbonate anions as the active phase. Carbon dioxide is present during the hydrolysis reaction (it is a product of the hydrolysis reaction), and in the presence of carbon dioxide, hydroxides, carbonates and bicarbonates react as shown:

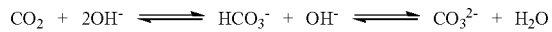

$$CO_2 + 2OH^- \rightleftharpoons HCO_3^- + OH^- \rightleftharpoons CO_3^{2-} + H_2O$$

Therefore, hydroxide and carbonate salts can act as a source of bicarbonate anions.

The initial charge of the carboxylation catalyst and the initial charge of the hydrolysis catalyst catalyse the reaction of alkylene oxide with carbon dioxide, and catalyse the reaction of alkylene carbonate with water. If one or both of the catalysts are homogeneous, the process preferably uses a catalyst recycle loop whereby catalyst is separated from the alkylene glycol product and is recycled so that it is combined with the alkylene oxide reactant. An initial charge of homogeneous catalyst is preferably added by supplying a solution of the catalyst to the catalyst recycle loop such that the catalyst is combined with the alkylene oxide reactant. If both the carboxylation catalyst and the hydrolysis catalyst are homogeneous, then the catalysts are preferably supplied to the catalyst recycle loop as a solution comprising both of the catalysts. An initial charge of heterogeneous catalyst is added by packing the heterogeneous catalyst into a reactor where the carboxylation and/or the hydrolysis will occur. In one embodiment of the invention, heterogeneous carboxylation or heterogeneous hydrolysis catalysts are contained within two or more separate vessels arranged in parallel and wherein said vessels have associated switching means such that in operation the feed can be switched between the vessels.

The degradation and associated activity of the hydrolysis catalyst is monitored. For a homogeneous hydrolysis catalyst the degradation can be measured by taking samples, preferably from a recycle loop, and measuring the concentration of basic hydrolysis catalyst by acid/base titration. From the concentration of hydrolysis catalyst in the recycle loop it is possible to calculate the concentration of hydrolysis catalyst in the reactor, and the activity of the catalyst will be proportional to the concentration of hydrolysis catalyst in the reactor. Instead of determining the absolute concentration of the hydrolysis catalyst, it is also possible to monitor degradation by measuring the change in ratio of hydrolysis catalyst to carboxylation catalyst, again by taking samples from a recycle loop and carrying out acid/base titration. The relative amount of hydrolysis catalyst will decrease as the hydrolysis catalyst degrades, and the associated activity of the hydrolysis catalyst will also decrease. For a heterogeneous catalyst wherein the active species are basic anions, the degradation can be measured by taking a sample of the heterogeneous catalyst, measuring the concentration of basic anions by titration and comparing this with the concentration of basic anions in a sample of fresh catalyst. Alternatively, the degradation can be measured by switching reactor vessels packed with heterogeneous catalyst, regenerating the heterogeneous catalyst by passing a solution comprising basic anions through the catalyst bed, and measuring the quantity of basic anions removed from the solution during the regeneration. For other types of heterogeneous catalyst, e.g. basic alumina, the degradation can be measured by switching reactor vessels packed with heterogeneous catalyst and monitoring the relative activity of fresh and used beds (activity can be assessed by taking samples of the product stream and analysing the samples using standard techniques).

Monitoring of the degradation of the hydrolysis catalyst is preferably carried out at least once every week and more preferably is carried out every day.

When the activity of the hydrolysis catalyst has fallen below a minimum level, an additional charge of the hydrolysis catalyst is added. When the hydrolysis catalyst is a homogeneous catalyst, a preferred way of assessing whether the activity of the hydrolysis catalyst has fallen below a minimum level is to set a minimum concentration of hydrolysis catalyst that must be present in the recycle stream. When the hydrolysis catalyst is a heterogeneous catalyst, a preferred way of assessing whether the activity of the hydrolysis catalyst has fallen below a minimum level is to set a minimum conversion that must be achieved by a reactor vessel containing hydrolysis catalyst.

When the activity of hydrolysis catalyst has fallen below the minimum level, an additional charge of the hydrolysis catalyst is added. If an additional charge of carboxylation catalyst is added when the additional charge of the hydrolysis catalyst is added, the weight ratio of additional hydrolysis catalyst to additional carboxylation catalyst is at least 5:1, preferably at least 10:1, more preferably at least 50:1. Most preferably, the addition charge of the hydrolysis catalyst is added without adding any additional carboxylation catalyst. If the hydrolysis catalyst is homogeneous, the additional charge of catalyst is preferably added by supplying a solution of the hydrolysis catalyst to the catalyst recycle loop. The additional charge does not have to be the same catalyst compound as the initial charge. For example, the initial charge can be a potassium carbonate solution and the additional charge(s) can be potassium hydroxide solution. If the hydrolysis catalyst is heterogeneous, the additional charge of catalyst is preferably added by replacing the used heterogeneous catalyst with fresh heterogeneous catalyst. A simple way to achieve this is to have heterogeneous hydrolysis catalysts contained within two or more separate vessels arranged in parallel, wherein said vessels have associated switching means such that in operation the feed can be switched between the vessels. The heterogeneous catalyst can be replaced with fresh heterogeneous catalyst by switching the feed to a vessel containing fresh catalyst. Degraded heterogeneous catalyst wherein the heterogeneous comprises basic anions on a support can be regenerated by treatment with a solution of basic anions.

When the hydrolysis catalyst is a homogeneous catalyst, there is likely to be a desirable upper limit on the concentration of the hydrolysis catalyst. The inventors have discovered that as the concentration of hydrolysis catalyst increases, the degradation of carboxylation catalysts such as halogenated organic phosphonium or ammonium salts, can also increase. Therefore, when an additional charge of the hydrolysis catalyst is added, the amount of additional catalyst is preferably such that the total concentration of hydrolysis catalyst will not be above an upper limit. This limit can be determined by observing how the carboxylation degrades as the hydrolysis catalyst concentration increases.

In a conventional process it would be usual to replenish both the carboxylation catalyst and the hydrolysis catalyst at regular intervals. The present invention differs in that it has been recognised that it is beneficial to provide additional hydrolysis catalyst when not providing additional carboxylation catalyst (or at least by providing a significant excess of hydrolysis catalyst to carboxylation catalyst). In the present invention steps (b) and (c) are preferably operated continually, e.g. monitoring of the hydrolysis catalyst is daily or weekly, and addition of additional hydrolysis catalyst occurs as necessary. However, after a period of monitoring and addition of hydrolysis catalyst, e.g. after several weeks or months of monitoring and several additional charges of hydrolysis catalyst, it may then be preferable to add additional charges of both carboxylation catalyst and hydrolysis catalyst. For example, step (c) may be carried out three or more times before additional charges of hydrolysis catalyst and carboxylation catalyst are added.

FIG. 1 shows a preferred embodiment of the process of the invention. The apparatus includes a carboxylation reactor (1), a hydrolysis reactor (5) and a distillation column (7). Carbon dioxide (2) is fed to the carboxylation reactor. Ethylene oxide and water (3) are also fed to the carboxylation reactor. An initial charge of homogeneous carboxylation catalyst and an initial charge of homogeneous hydrolysis catalyst are fed (10) to a line that feeds into the ethylene oxide and water feed line (3). This catalyses the carboxylation reaction. A reaction stream comprising ethylene carbonate produced in the carboxylation reactor (1), and also comprising carboxylation catalyst and hydrolysis catalyst is fed (4) to the hydrolysis reactor (5). The hydrolysis catalyst catalyses the reaction of ethylene carbonate to ethylene glycol in the hydrolysis reactor (5). The product stream from the hydrolysis reactor (5) is fed (6) to a distillation column (7). Glycol products (8) are extracted from the distillation column (7) and a catalyst solution of carboxylation catalyst and hydrolysis catalyst is fed (9) back to the ethylene oxide and water feed line (3). The concentration of the hydrolysis catalyst is measured every day by taking samples from the recycle loop (9). Acid/base titration of the samples provides a measurement of the concentration of the hydrolysis catalyst. When the concentration of hydrolysis catalyst falls below a minimum level, an additional charge of the homogeneous hydrolysis catalyst is added at point (10) (and no further carboxylation catalyst is added).

The following examples are illustrative but not limiting of the invention.

Effect of Hydrolysis Catalyst Concentration

A number experiments were performed with different amounts of hydrolysis catalyst in order to illustrate the invention. Lower amounts of hydrolysis catalyst illustrate the circumstance where degradation of the hydrolysis catalyst has occurred. Higher amounts of hydrolysis catalyst illustrate the circumstance where additional hydrolysis catalyst has been added such that the concentration of hydrolysis catalyst is above a preferred limit.

The experiments are described making use of the process outline of FIG. 1. Batch autoclave experiments were performed in order to mimic process conditions {temperature, pressure, catalyst composition, etc) in process apparatus (the hydrolysis reactor (5) and distillation column (7)) with contents representing the various process streams. In general the various process streams in the process apparatus and in the process lines contain the following components:

Carboxylation reactor (1): ethylene oxide/ethylene carbonate/water/carboxylation catalyst/hydrolysis catalyst/$CO_2$ Line (4): ethylene carbonate/water/carboxylation catalyst/hydrolysis catalyst/$CO_2$ Hydrolysis reactor (5): ethylene carbonate/monoethylene glycol/water/carboxylation catalyst/hydrolysis catalyst/$CO_2$ Line (6): monoethylene glycol/water/carboxylation catalyst/hydrolysis catalyst Distillation column (7): monoethylene glycol/water/carboxylation catalyst/hydrolysis catalyst In carboxylation reactor (1), ethylene oxide is converted into ethylene carbonate under the influence of the carboxylation catalyst.

In hydrolysis reactor (5), ethylene carbonate is converted into monoethylene glycol under the influence of the hydrolysis catalyst.

In distillation column (7) glycols (mainly monoethylene glycol, some diethylene glycol) and water are separated from both catalysts (a 20-70% wt solution in monoethylene glycol/diethylene glcyol).

Example 1a-c

In this experiment the effect of the amount of a commonly used basic hydrolysis catalyst ($K_3PO_4$) in the presence of a commonly used carboxylation catalyst (KI) on by-product formation (e.g. formation of 2-methyl-1,3-dioxolane) and selectivity to monoethylene glycol (assessed by the formation of a higher glycol diethylene glycol) is evaluated under conditions representative for hydrolysis reactor (5) and with a composition representative for the process stream of line (4) and the contents of reactor (5).

Table 1 shows the conditions for experiments 1a-1c:

TABLE 1

|  | Exp 1a | Exp 1b | Exp 1c |
| --- | --- | --- | --- |
| Water (g) | 20 | 20 | 20 |
| Monoethylene glycol (g) | 20 | 20 | 20 |
| Ethylene carbonate (g) | 40 | 40 | 40 |
| KI (g) | 3.9 | 3.9 | 3.9 |
| KI (mol/l) | 0.30 | 0.30 | 0.30 |
| $K_3PO_4$ (g) | 0.04 | 0.09 | 0.42 |
| $K_3PO_4$ (mol/l) | 0.003 | 0.005 | 0.025 |
| Temperature (° C.) | 150 | 150 | 150 |
| $CO_2$ pressure (barg) | 20 | 20 | 20 |
| Time (h) | 4 and 6 | 4 | 4 |

After 4 h (and for experiment 1a also after 6 h, because of the slower ethylene carbonate hydrolysis) the resulting mixtures were analyzed by GC analysis. The results are shown in Table 2:

TABLE 2

| Component | Exp 1a @ 4 h | Exp 1a @ 6 h | Exp 1b @ 4 h | Exp 1c @ 4 h |
| --- | --- | --- | --- | --- |
| Ethylene carbonate (% wt) | 0.41 | 0.04 | 0.07 | 0.007 |
| Monoethylene glycol (% wt) | 75.9 | 76.3 | 76.4 | 75.7 |
| Diethylene glycol (% wt) | 0.73 | 0.78 | 0.48 | 0.18 |
| Diethylene glycol (ppm) | 7341 | 7774 | 4831 | 1821 |
| 2-methyl-1,3-dioxolane (ppm) | 298 | 310 | 173 | 33 |

These results clearly demonstrates that low hydrolysis catalyst concentration (which could result from degradation of the hydrolysis catalyst and failure to add additional hydrolysis catalyst) results not only in slow hydrolysis of ethylene carbonate, but also in more undesired by-product formation (e.g. 2-methyl-1,3-dioxolane) and in worse monoethylene glycol selectivity (100%*MEG/(MEG+DEG)). In the present invention, the activity of the hydrolysis catalyst is monitored and further hydrolysis catalyst is added when the activity falls below a specified level. This avoids the slow hydrolysis, high by-product formation and poor selectivity illustrated by this experiment.

Example 2a-c

In this experiment the effect of the amount of a commonly used basic hydrolysis catalyst 2 (KOH) on the stability of a commonly used carboxylation catalyst, tetra-n-propylammoniumiodide (TPAI) is evaluated under conditions representative for distillation column (7) and with a composition representative for the process stream in line (6) and the contents of column (7).

Table 3 shows the conditions for experiments 2a-2c:

TABLE 3

|  | Exp 2a | Exp 2b | Exp 2c |
| --- | --- | --- | --- |
| Water (g) | 11 | 11 | 11 |
| Monoethylene glycol (g) | 47 | 47 | 47 |
| TPAI (g) | 2.3 | 2.3 | 2.3 |
| TPAI (mol/l) | 0.12 | 0.12 | 0.12 |
| KOH (g) | 0.02 | 0.34 | 1.74 |
| KOH (mol/l) | 0.006 | 0.10 | 0.49 |
| Temperature (° C.) | 160 | 160 | 160 |
| $N_2$ pressure (barg) | 20 | 20 | 20 |
| Time (h) | 22 | 22 | 22 |

After 22 h the resulting mixture was analyzed by $^{13}C$ NMR; TPAI catalyst degradation is visible by a decline in TPAI content and the formation of TPA (tri-n-propylamine), which is a TPAI degradation product. The results are shown in Table 4:

TABLE 4

|  | Exp 2a | Exp 2b | Exp 2c |
| --- | --- | --- | --- |
| TPA formation | No | Yes | Yes |
| Decrease in TPAI content (%) | 4 | 43 | 91 |

These results demonstrate that high hydrolysis catalyst concentration (which could result from adding too much hydrolysis catalyst after degradation of hydrolysis catalyst has been detected) can have a detrimental effect on the stability of the carboxylation catalyst. In a preferred embodiment of the present invention, when an additional charge of the hydrolysis catalyst is added, the amount of additional catalyst is preferably such that the total concentration of hydrolysis catalyst will not be above an upper limit. This avoids the degradation of carboxylation catalyst illustrated by this experiment.

Example 3a-c

In this experiment the effect of the amount of a commonly used basic hydrolysis catalyst (KOH) on the stability of a commonly used carboxylation catalyst, tetra-n-butylphosphoniumbromide, (TBPB) is evaluated under conditions representative for distillation column (7) and with a composition representative for the process stream of line (6) and the contents of column (7).

Table 5 shows the conditions for experiments 3a-3c:

TABLE 5

|  | Exp 3a | Exp 3b | Exp 3c |
| --- | --- | --- | --- |
| Water (g) | 11 | 11 | 11 |
| Monoethylene glycol (g) | 47 | 47 | 47 |
| TBPB (g) | 22.5 | 23.3 | 24.7 |
| TBPB (mol/l) | 0.80 | 0.80 | 0.80 |
| KOH (g) | 1.40 | 3.37 | 7.14 |
| KOH (mol/l) | 0.30 | 0.70 | 1.40 |
| Temperature (° C.) | 165 | 165 | 165 |
| $N_2$ pressure (barg) | 12.5 | 12.5 | 12.5 |
| Time (h) | 193 | 193 | 193 |

After 193 h the resulting mixture was analyzed by $^{31}P$ NMR; TBPB catalyst degradation is visible by a decline in TBPB content and the formation of TBPO (tri-n-butylphosphine oxide), which is a TBPB degradation product. The results are shown in Table 6:

TABLE 6

|  | Exp 2a | Exp 2b | Exp 2c |
|---|---|---|---|
| TBPO formation | Yes | Yes | Yes |
| Decrease in TBPB content (mol %) | 0.8 | 2.3 | 18.1 |

Again, these results demonstrate that high hydrolysis catalyst concentration (which could result from adding too much hydrolysis catalyst after degradation of hydrolysis catalyst has been detected) can have a detrimental effect on the stability of the carboxylation catalyst. In a preferred embodiment of the present invention, when an additional charge of the hydrolysis catalyst is added, the amount of additional catalyst is preferably such that the total concentration of hydrolysis catalyst will not be above an upper limit. This avoids the degradation of carboxylation catalyst illustrated by this experiment.

What is claimed is:

1. A process for the preparation of an alkylene glycol from an alkylene oxide, wherein alkylene oxide reacts with carbon dioxide in the presence of a carboxylation catalyst to provide alkylene carbonate, wherein alkylene carbonate reacts with water in the presence of a hydrolysis catalyst to provide alkylene glycol, and wherein the active phase of the hydrolysis catalyst is one or more bases, comprising steps of
   (a) adding an initial charge of the carboxylation catalyst and an initial charge of the hydrolysis catalyst to catalyse the reaction of alkylene oxide with carbon dioxide, and to catalyse the reaction of alkylene carbonate with water;
   (b) monitoring the degradation and activity of the hydrolysis catalyst; and
   (c) when the activity of the hydrolysis catalyst has fallen below a minimum level, adding an additional charge of the hydrolysis catalyst, wherein if an additional charge of carboxylation catalyst is added when the additional charge of the hydrolysis catalyst is added, the weight ratio of additional hydrolysis catalyst to additional carboxylation catalyst is at least 5:1.

2. The process of claim 1 wherein no additional carboxylation catalyst is added when the additional charge of hydrolysis catalyst is added.

3. The process of claim 2 wherein the hydrolysis catalyst is homogeneous.

4. The process of claim 1 wherein the hydrolysis catalyst is homogeneous.

5. The process of claim 1 wherein the hydrolysis catalyst and the carboxylation catalyst are homogeneous.

6. The process of claim 1 wherein the process uses a catalyst recycle loop whereby hydrolysis catalyst and carboxylation catalyst are separated from the alkylene glycol product and are recycled so that they are combined with the alkylene oxide, wherein the initial charge of hydrolysis catalyst and the initial charge of carboxylation catalyst are added by supplying a solution comprising the hydrolysis catalyst and the carboxylation catalyst to the catalyst recycle loop and wherein the additional charge of hydrolysis catalyst is added by supplying a solution of the hydrolysis catalyst to the catalyst recycle loop.

7. The process of claim 6 wherein the degradation of the hydrolysis catalyst is measured by taking samples from the recycle loop, and measuring the concentration of hydrolysis catalyst by acid/base titration.

8. The process of claim 1 wherein the hydrolysis catalyst is heterogeneous.

9. The process of claim 8 wherein the heterogeneous hydrolysis catalyst is contained within two or more separate vessels arranged in parallel, wherein said vessels have associated switching means such that in operation feed can be switched between the vessels and wherein the additional charge of hydrolysis catalyst is added by switching the feed to a vessel containing fresh catalyst.

10. The process of claim 9 wherein the degradation of the hydrolysis catalyst is measured by switching reactor vessels and monitoring the relative activity of fresh and used catalyst beds.

11. The process of claim 1 wherein the hydrolysis catalyst has bicarbonate anions as the active phase.

12. The process of claim 1 wherein if an additional charge of carboxylation catalyst is added when the additional charge of the hydrolysis catalyst is added, the weight ratio of additional hydrolysis catalyst to additional carboxylation catalyst is at least 10:1.

13. The process of claim 12 wherein if an additional charge of carboxylation catalyst is added when the additional charge of the hydrolysis catalyst is added, the weight ratio of additional hydrolysis catalyst to additional carboxylation catalyst is at least 50:1.

* * * * *